United States Patent [19]
Hansen

[11] 3,994,421
[45] Nov. 30, 1976

[54] UNITARY THERAPEUTIC AEROSOL DISPENSER

[75] Inventor: Lloyd Frank Hansen, Campbell Hall, N.Y.

[73] Assignee: American Cyanamid Company, Stamford, Conn.

[22] Filed: Sept. 29, 1975

[21] Appl. No.: 617,339

[52] U.S. Cl. .............................. 222/182; 128/225; 222/402.13
[51] Int. Cl.² ......................................... A61M 15/02
[58] Field of Search ............ 239/587, 337; 128/203, 128/225, 208, 266; 222/402.2, 402.13, 402.16, 182, 192, 402.1

[56] References Cited
UNITED STATES PATENTS

| | | | |
|---|---|---|---|
| 2,985,382 | 5/1961 | Coplan | 222/182 X |
| 3,001,524 | 9/1961 | Maison et al. | 222/402.2 X |
| 3,559,851 | 2/1971 | Steiman | 222/402.2 |
| 3,768,475 | 10/1973 | Osborne | 128/225 |
| 3,809,294 | 5/1974 | Torgeson | 222/182 |
| 3,900,138 | 8/1975 | Phillips | 239/338 X |

Primary Examiner—Allen N. Knowles
Assistant Examiner—Norman L. Stack, Jr.
Attorney, Agent, or Firm—Samuel Branch Walker

[57] ABSTRACT

A combination aerosol container carrier and deceleration chamber carries an aerosol container interiorly of the deceleration chamber and by pulling out and, pivoting the aerosol container in its case, is changed to a dispensing configuration in such a manner that essential parts are not apt to be dropped and incorrect assembly is avoided even when the user is under stress or adverse environmental conditions. The dispenser provides for unitary doses of inhalable medicament, with uniform doses and very convenient administration.

1 Claim, 4 Drawing Figures

UNITARY THERAPEUTIC AEROSOL DISPENSER

BACKGROUND OF THE INVENTION

Therapeutic aerosol dispensing systems have been known for some time that, using metering dispensing systems, have dispersed small particles for inhalation into the lungs. Uniform doses are very much desired.

Because inhalation therapy is frequently required for patients who may have defective vision, or be old or feeble or hurried; so that administration needs to be accomplished under adverse conditions of illumination, or under time pressure by persons whose vision and motor control is impaired; it is desirable that a dispenser be simple to operate and preferably of such construction that the dispenser can be assembled in only one fashion.

Preferably all essential parts are fastened together so that essential pieces cannot be misplaced during use. For instance the patient may desire to use his dispenser during an asthma attack when his concentration and motor coordination is impaired. The patient may need to administer a drug for asthma treatment very rapidly once an attack occurs. It is highly desirable that the patient not be frustrated with a complex assembly operation to prepare a dispenser for administration.

SUMMARY OF THE INVENTION

The present invention incorporates a construction permitting assembling an aerosol container to a dispenser having a deceleration chamber in which the aerosol container is stored during transportation and which, by withdrawing the container in a container case, opens up the deceleration chamber and by pivoting with respect to the deceleration chamber locks the assembly into a fixed position which is particularly convenient for the administration of the medicament in the aerosol container.

DESCRIPTION OF PRIOR ART

Certain representative patents in this very crowded field include:

U.S. Pat. Nos. 2,721,010 - Meshberg, Oct. 18, 1955, AEROSOL CONTAINERS AND VALVES THEREFOR, and 2,968,427 Meshberg, Jan. 17, 1961, VALVE FOR AEROSOL CONTAINER, show metering valves for aerosol containers. Small uniform charges of the contents are dispensed on each separate actuation.

Such valves, among others, may be used for metering doses for the present invention.

U.S. Pat. No. 2,992,645 - Fowler, July 18, 1961, DISPENSER FOR POWDERS, in Column 2 has a table showing the effect of particle size on the zone of deposition of a powder in the respiratory tract. Powder sizes of 1 and 3 microns are shown to go deeply into the lungs.

U.S. Pat. No. 3,012,555 - Meshberg, Dec. 12, 1961, DISPENSING PACKAGE FOR MATERIAL UNDER PRESSURE, shows an aerosol liquid dispenser with an operating button assembled to the valve system, which button, with spray orifice, fits removably into an applicator nozzle. In one configuration the applicator nozzle is used for spray control; in another for protective storage.

U.S. Pat. No. 3,219,533 - Mullins, Nov. 23, 1965, AEROSOL SOLID MEDICAMENT IN PROPELLANT AND LOW-LEVEL ETHANOL AVOIDING HIGHER LEVEL ETHANOL DISPERSED-SOLID REFLOCCULATION, shows many solid medicaments, including such steroids as hydrocortisone, prednisolone and dexamethasone dispersed in the particle size range of 0.5 to 10 microns in certain chlorofluoroalkanes using 0.5 to 5.0 percent ethanol, for inhalation and ophthalmic therapy.

U.S. Pat. No. 3,236,458 - Ramis, Feb. 22, 1966, AEROSOL APPARATUS, shows an aerosol liquid dispenser using coaxial concentric extendable tubes for particle size control.

U.S. Pat. No. 3,727,806 - Wilmot, Apr. 17, 1973, VALVE ASSEMBLIES FOR AEROSOL CONTAINERS, shows a metering valve assembly in which a hollow member fits over the inner end of the valve stem and moves therewith to create a capillary gap to aid in avoiding wastage as the container contents become exhausted. This container is used in a valve down position.

U.S. Pat. No. 3,809,294 - Torgeson, May 7, 1974, DISPENSING LUNG CONTACTING POWDERED MEDICAMENTS shows a combination aerosol carrier and deceleration chamber in which the aerosol container is taken out of the deceleration chamber and reassembled in dispensing configuration. This patent discloses prior art, examples of medicaments and a dispensing container. Said U.S. Pat. No. 3,809,294, is hereby herein incorporated by this reference thereto. The present invention is an improvement over the inhaling dispenser shown in U.S. Pat. No. 3,809,294.

U.S. Pat. No. 3,895,111 - Corey, Barringer and Hansen, July 15, 1975, ASTHMA TREATMENT BY INHALATION OF MICRONIZED N,N-DIETHYL-4-METHYL-1PIPERAZINECARBOXAMIDE PAMOATE, shows an inhaler with a specific therapeutic agent.

U.S. Pat. No. 3,897,779, Hansen, Aug. 5, 1975, TRIAMCINOLONE ACETONIDE INHALATION THERAPY, described an inhaler, and triamcinolone acetonide as a therapeutic agent.

U.S. Pat. No. 3,184,115 - Meshberg, May 18, 1965, AEROSOL DISPENSING PACKAGE shows a telescoping pivoting sleeve which acts as a spray directing shield, which is closed by a dust cap.

DRAWINGS

Figure 1:
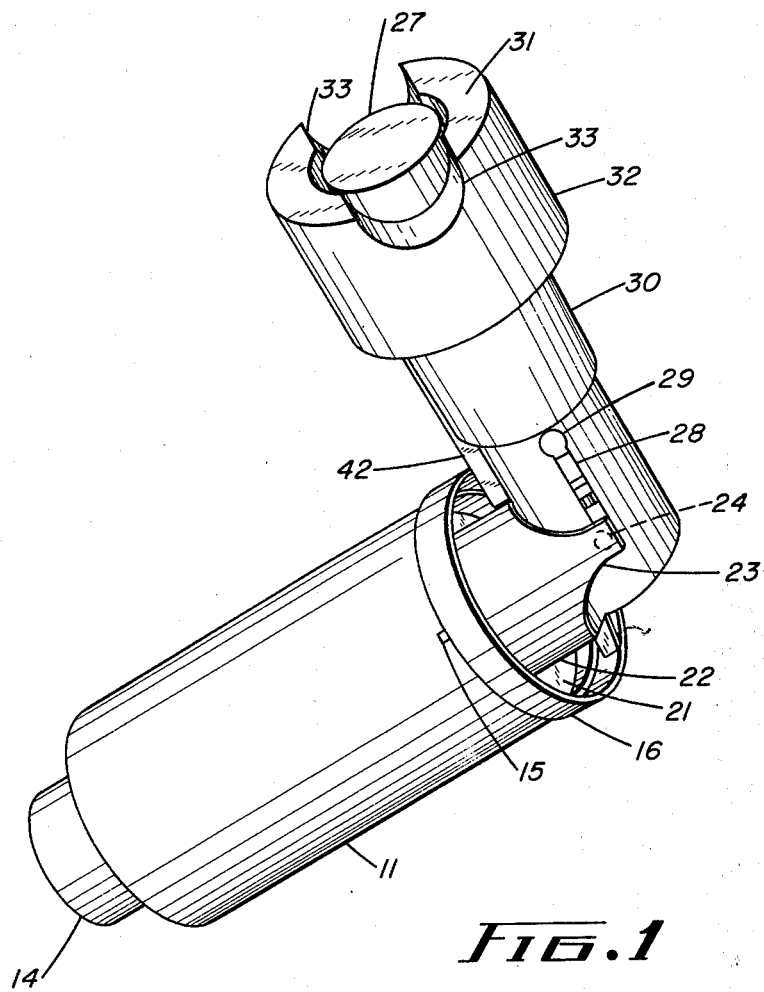
FIG. 1 is a pictorial view of the aerosol dispenser in dose administering configuration.
Figure 2:
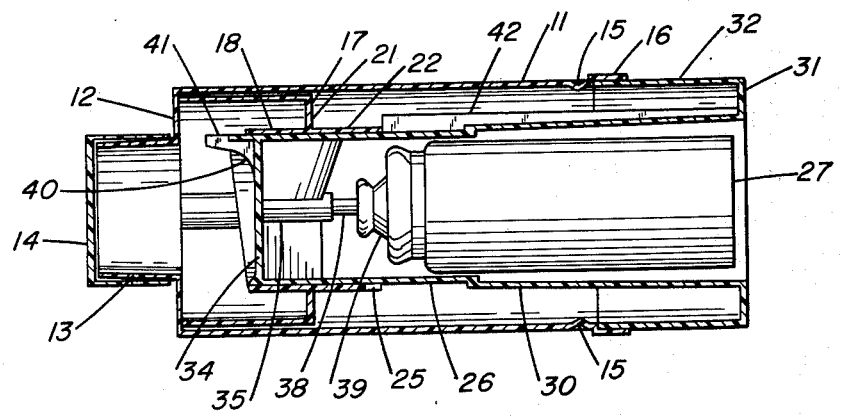
FIG. 2 is a view in partial section of the aerosol dispenser in the storage and transportation configuration.
Figure 3:
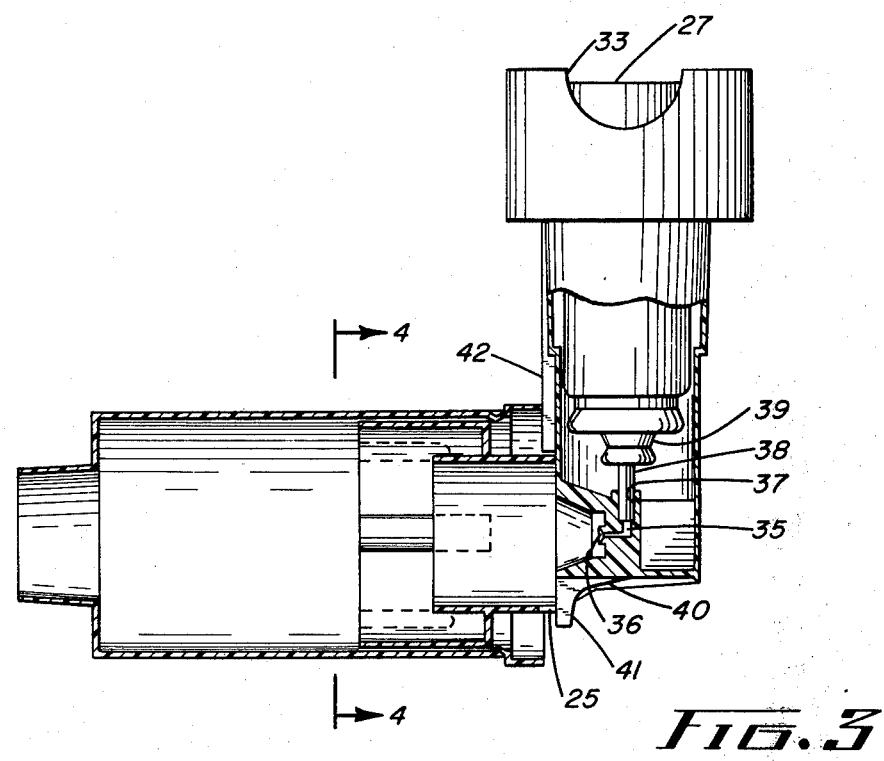
FIG. 3 is a view in partial section of the aerosol dispenser in dose administration configuration.
Figure 4:
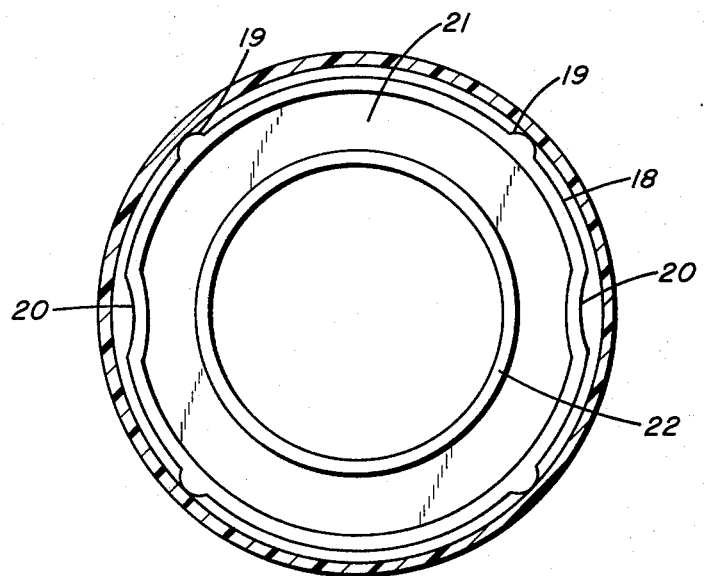
FIG. 4 is a cross-section at cutting plane 4—4 through the cylindrical barrel showing the piston assembly in end view.

As shown in FIG. 1 the present aerosol dispenser in one configuration is extended and folded for administration of a medicament suspended in an aerosol propellant, and as shown in FIG. 2 the aerosol dispenser may be collapsed for storage so that the collapsed device may be placed in a pocket or purse for storage until time of use. A view in partial section in collapsed form, FIG. 2, shows the various parts particularly clearly. The cylindrical barrel 11 has the dual functions of a carrier cylindrical container carrier during the transportation configuration and a deceleration chamber during the use configuration. At one end of the cylindrical barrel 11 is an end wall 12 in which is formed a mouthpiece 13. In storage configuration a mouthpiece cap 14 fits over the mouthpiece and protects the contents of the dispenser from dust. The mouthpiece cap can fit inside of or outside of the mouthpiece and is preferably of as small a size as is compatible with its functions. Conveniently, but not necessarily, the cylindrical barrel can be approximately 1-158 inches in diameter and 2-182 inches long with the mouthpiece being about seven-eighths of an inch in diameter. Such dimensions are not critical. The mouthpiece needs to be large enough to fit readily into the human mouth whether the user is a child or an adult. The size of the deceleration chamber is a compromise between a chamber of which is large enough to receive a dispensed dose of the medicament and permit larger particles to settle out and for the entire charge to lose its velocity, and yet is small enough to conveniently fit into the pocket of the user.

Adjacent to the other end of the cylindrical barrel 11 are piston stops 15. At least one piston stop is needed, two are shown, and more can be used. The piston stops are formed by dimpling the cylinder walls to give piston stops interiorly of the cylindrical barrel to aid in controlling the position of a piston as described later. Attached to and extending beyond the barrel for a short distance is a barrel extension 16, which is slightly larger in diameter than the cylindrical barrel itself, and serves as a retainer for a case flange 32 as described later. Conveniently the cylindrical barrel 11 together with the end wall, mouthpiece, piston stops, and barrel extension is formed by molding a single piece of plastic in a suitably shaped injection mold with the exception that the piston stops are dimpled into the cylindrical barrel after the molding is complete to permit the more convenient removal of that portion of the mold which forms the interior of the barrel.

Inside of the cylindrical barrel 11 is a piston 17. The piston is slightly smaller than the barrel and is mounted interiorly in the barrel so as to be slidable therein. A piston skirt 18 fits inside of the cylindrical barrel 11 and is long enough to prevent the piston from cocking in the barrel. A length of about one half of its diameter gives good control. Friction rails 19 are molded in the outside of the skirt so as to slide interiorly of the cylindrical barrel and minimize friction. The piston skirt is slightly smaller than the cylindrical barrel and by having the raised rails air bleeds between the piston skirt 18 and the cylindrical barrel and serves as a source of diluent air when the device is used.

The use of friction rails 19 also permits the piston to fit sufficiently loosely in the cylindrical barrel 11 that the cylindrical barrel may have a slight taper. While not functionally desirable during use, unless the cylindrical barrel has a slight taper, the molding becomes a more expensive problem. A very slight taper permits the molding pin to be withdrawn from the cylindrical barrel. A slight draft or using a very slightly conical barrel rather than a true cylinder is quite customary in the molding arts. Whenever possible the molded plastic parts are designed to permit this slight taper. Surprisingly, by using the friction rails enough taper is permitted for both inexpensive manufacture and convenience in use.

Also formed in the piston skirt are index grooves 20. These index grooves 20 cooperate with the positioning stops 15 so that by twisting the piston until the index grooves align with the piston stops, the piston may be inserted in the cylindrical barrel during assembly, and then by turning the piston 17 slightly, removal of the piston is prevented unless and until the indexing grooves are carefully oriented with the piston stops. During normal use the piston is pulled out until the piston stops are reached at which point the piston is held in its rear most operating position.

A piston head 21 partialy closes the rear end of the piston. Axially in said piston head is a telescoping sleeve 22. Two telescoping sleeve arms 23 extend rearwardly from the main sleeve and have towards the rear ends thereof headed retention studs 24. These retention studs point inwardly towards each other and form a pivot axis for a container case 26 as later described. By having a head on the studs like the head on a nail, the retention studs may only be inserted or withdrawn at the point of enlargement in the stud channels 28 later described.

On one side of the sleeve 22 between the telescoping sleeve 23 arms, is a vane aligning slot 25.

A container case 26 telescopically fits into the telescoping sleeve 22. The container case is of such size as to enclose and contain an aerosol container 27. The front end of the container case slides in the telescoping sleeve. During the storage configuration the container case fits well forward in the telescoping sleeve. This permits conserving space an having a comparatively large aerosol container 27 within a pocketable size dispenser. In the sides of the container case 26 are stud channels 28. At the rear end of the stud channels 28 are the stud insertion apertures 29. When assembled to telescoping sleeve arms 23, the headed retention studs fit through the stud channels and permit telescoping of the container case into the telescoping sleeve during the storage configuration and permits withdrawal of the container case 26 to a dispensing position. The stud insertion apertures 29 permit assembly of the container case to the telescoping sleeve and prevent accidental disassembly. Intermediate of the length of the container case is an enlarged diameter of the container case 30 which prevents the container case from telescoping undesirably far into the telescoping sleeve. This enlarged diameter of the container case 30 abuts against the ends of the telescoping sleeve arms in the forward position.

At the rear of the case is a case base 31, around the outside of which is the case flange 32 which is cylindrical in general configuration to fit into a slide into the barrel extension 16 in the carrying configuration. By being of such size as to fit into the barrel extention, in closed configuration the rear end of the assembly is effectively sealed against the entrance of stray dirt.

Two finger ports 33 are formed in the case base 31, container case 26 and case flange 32 so that an aerosol container 27 inserted into the container case may be grasped between a finger and the thumb and pulled from the case.

At the front end of the case there is a case head 34 which has therein a spray nozzle 35 which includes a spray orifice 36 which spray orifice is at right angles to the axis of the case and connected to said nozzle. An actuating tube bore 37 receives the actuating tube 38 of a valve 39 on an aerosol container 27. The valve for the aerosol container is any of the conventional axially operated dose dispensing valves well known to the art. Also part of the case head 34 is a finger rest 40, which serves as a rest for the finger of the operator when actuating by pressing the container into the case, and also extends upward on the nozzle side of the container cae. Integral with this finger rest is a spray direction vane 41 which indicates the direction of the spray orifice 36 and also, with the finger rest, serves to prevent the bending of the case backwards with respect to the sleeve and controls the direction so that the spray nozzle can point in only one direction when the container case is bent with respect to the telescoping sleeve. Additionally this vane extends high enough so that in bending to the dispensing position the spray direction vane 41 fits into the vane aligning slot 25 giving additional directional support to prevent lateral twisting of the container case with respect to the telescoping sleeve.

On the same side, under the nozzle, is a case rest 42 which additionally serves to prevent the telescoping sleeve from bending more than 90° with respect to the container case so that in the dispensing position the spray nozzle is directed axially of the cylindrical barrel and locked against too great a rotation by the case rest as well as the configuration of the telescoping sleeve with respect to the telescoping sleeve arms and the side of the container case.

In storage the mouthpiece cap 14 rests over the mouthpiece and keeps dust from the front end of the dispenser, the case flange 32 cooperates with the barrel extension 16 so as to lock the back end to keep out dust and contaminants and give a solid pocketable dispenser.

At the time of use the mouthpiece cap is removed and if lost does not interfere with the dispensing of the medicament. All of the other pieces are more difficult to disassemble so that the risk of loss is negligible. The case flange is pulled rearwardly until the piston reaches the piston stops at which position the container case can be bent in only one direction, which by a bend of 90°, aligns the spary orifice 36 with the cylindrical barrel and causes the spray to enter axially into the cylindrical barrel. The locking against lateral motion by the spray direction vane 41 locking into the vane aligning slot 25 gives lateral stability so that in the dispensing configuration the dispenser has a solid positive feel, which permits the user to more readily press the aerosol container 27 against the actuating tube bore and cause a uniform single dose to be dispensed interiorly of the cylindrical barrel. The cylindrical barrel 11 together with its end wall 12 and the piston 17 in the rear position forms a deceleration chamber such that the medicament being sprayed is essentially brought to rest and forms an aerosol which is conveniently inhaled from the deceleration chamber with any large particles being permitted to settle out against the walls of the chamber, with uniformity of administration being obtained as set forth in Torgeson U.S. Pat. No. 3,809,294 supra.

The aerosol container 27 may be withdrawn when its contents are exhausted, and replaced with a filled aerosol container thus permitting the aerosol dispenser to be reused with additional aerosol containers as a refill.

Conveniently the aerosol dispenser and all of its parts are molded from a plastic such as polyethylene or polypropylene. If the working parts such as the telescope arms are of isotactic or high density prolypropylene and the case is of similar polypropylene, the dispenser has a longer useful life than if softer plastic are used. Wall thicknesses and proportions may be varied to fit the desires of a manufacturer. Inasmuch as most of the sections may be of approximity the same thickness, except for the spray nozzle and case head portions, manufacture is very convenient and conventional molding techniques give an excellent dispenser at a reasonable manufacturing cost.

As all of the parts are pivoted together, and the aersol container itself may be withdrawn but requires a positive grip between thumb and fore finger in the finger ports, the dispenser may be used by those whose physical condition at the time is either deteriorated or impaired, by an asthma attack or other syndrome, and hence the patient who would require an attendant to administer medication with prior art devices may safely be permitted to use the present device independently. For instance, with some types of prior art assemblies, the spray nozzle could be oriented to spray away from rather than towards the patient or a piece could be dropped during assembly, or the patient could have difficulty in aligning the nozzle with the mouthpiece assembly.

The present dispenser may thus be used under conditions of impaired ability and impaired motor control far more expeditiously and with much less risk of erroneous manipulation than is here been considered practical in an inexpensive device.

I claim:

1. An aerosol dispenser for dispensing uniform dosages of a finely-divided medicament suspended in a propellant at a low velocity in inhalable dry aerosol form in the particle size range of 0.5 to 10 microns, comprising:

a circular cylindrical container carrier and deceleration chamber consisting essentially of a cylindrical barrel, and at one end thereof an end wall, and a mouth piece in said end wall adapted to fit into a human mouth coaxil with the cylindrical barrel;

a mouthpiece cap, adapted to removably engage and close the mouthpiece in dust including relationship;

and adjacent the other end of the barrel, formed in the wall of the barrel, at least one piston stop, and attached to and extending beyond the barrel, a short barrel extension, coaxial with and slightly greater in diameter than the barrel;

a piston slightly smaller than said barrel, mounted interiorly of said barrel, and slideable therein, having a piston skirt of sufficient length to prevent the piston from cocking in the barrel, friction rails integral with and elevated above the surface of the piston skirt to slide in contact with and reduce friction with the barrel said piston having at least one indexing groove therein to cooperate with said piston stop, to permit the piston to be inserted in a groove oriented relationship only and when the piston is rotated, to retain the piston within the barrel; a piston head on said piston, and axially in said head a telescoping sleeve passing through the piston, two sleeve arms, extending rearward from the piston head, a headed retention stud on each arm, pointing inwardly towards each other, and said sleeve having a vane aligning slot therein between said arms;

a container case, the front end of which slideably telescoping fits in said telescoping sleeve, and the front part of which case has therein two opposed stud channels, the main portions of which are adapted to slideably hold the retention studs, and the rear end of which channels are enlarged to pass the heads on the studs so that the heads may be inserted or removed only when the studs are at the rear end of travel in said channels; an enlarged diameter of the container case intermediate of the length of the container case which limits the forward engagement of the case into the sleeve, a case at the rear end of the case, a case flange on the case base, cylindrical in shape and of such size as to fit into and be held by the barrel extension in a closed position; two finger ports in the case base and case flange, whereby an aerosol container inserted into the case may be grasped between the finger and thumb and removed from the case; at the front end of the case, a spary nozzle having a spray orifice therein, which sprays at right angles to the axis of the case, and connected to said nozzle, an actuating tube bore to receive the actuating tube of a valve on an aerosol container, whereby when an aerosol valve on the container engages and is operated by the actuating tube bore, a metered dose of medicament is dispensed through thus spray nozzle;

a case rest on the side of the case, which locks against the sleeve when the case is bent to dispensing position to hold the maximum bending between case and sleeve to 90°, a case head at the front end of the case, having a raised finger rest which both provides a rest for the operator's finger when actuating by pressing a container into the case, and extends upward to prevent the bending of the case backwards with respect to the sleeve, and a spray direction vane on the case head, which indicates the direction of the spray nozzle, and locks into the vane aligning slot in the sleeve to give lateral stability to the assembly during use.

* * * * *

UNITED STATES PATENT OFFICE
CERTIFICATE OF CORRECTION

Patent No. 3,994,421　　　　　　　　　　Dated November 30, 1976

Inventor(s) LLOYD FRANK HANSEN

It is certified that error appears in the above-identified patent and that said Letters Patent are hereby corrected as shown below:

Column 7, line 3, insert -- base -- after "case", second occurrence.

*Signed and Sealed this*

Twenty-second *Day of* February 1977

[SEAL]

Attest:

RUTH C. MASON
*Attesting Officer*

C. MARSHALL DANN
*Commissioner of Patents and Trademarks*